(12) United States Patent
Baraldi et al.

(10) Patent No.: US 7,579,378 B2
(45) Date of Patent: Aug. 25, 2009

(54) SULFONAMIDO COMPOUNDS THAT ANTAGONIZE THE VANILLOID TRPV1 RECEPTOR

(75) Inventors: Pier Giovanni Baraldi, Ferrara (IT); Pier Andrea Borea, Ferrara (IT); Pierangelo Geppetti, Ferrara (IT)

(73) Assignee: Pharmeste S.R.L. (IT)

( * ) Notice: Subject to any disclaimer, the term of this patent is extended or adjusted under 35 U.S.C. 154(b) by 105 days.

(21) Appl. No.: 11/577,857

(22) PCT Filed: Oct. 18, 2005

(86) PCT No.: PCT/EP2005/011206
§ 371 (c)(1), (2), (4) Date: Nov. 29, 2007

(87) PCT Pub. No.: WO2006/045498
PCT Pub. Date: May 4, 2006

(65) Prior Publication Data
US 2009/0118374 A1    May 7, 2009

(30) Foreign Application Priority Data
Oct. 26, 2004   (IT) .......................... MI2004A2042

(51) Int. Cl.
A61K 31/17    (2006.01)
C07C 275/40   (2006.01)
C07C 275/24   (2006.01)
C07C 335/20   (2006.01)
C07C 335/12   (2006.01)

(52) U.S. Cl. .................. 514/586; 514/597; 514/595; 564/27; 564/49; 564/56

(58) Field of Classification Search .......... 514/586, 514/597, 595; 564/27, 49, 56
See application file for complete search history.

(56) References Cited

U.S. PATENT DOCUMENTS
7,067,553 B2 *  6/2006  Suh et al. .................... 514/476

FOREIGN PATENT DOCUMENTS
EP   0 693 386 A    1/1996
WO   WO 02/16318 A  2/2002

OTHER PUBLICATIONS
Shan, K.J. et al.: "Benzylthiourease. III" J. Indian Chem. Soc., 36, 507-8, 1959, XP009059692 p. 507, Table 1: p. 508, Table II.
International Search Report PCT/EP2005/011206 dated Jan. 11, 2006.

* cited by examiner

Primary Examiner—Peter G O'Sullivan
(74) Attorney, Agent, or Firm—Ostrolenk Faber LLP

(57) ABSTRACT

The invention relates to sulfonamido derivatives of formula (I)

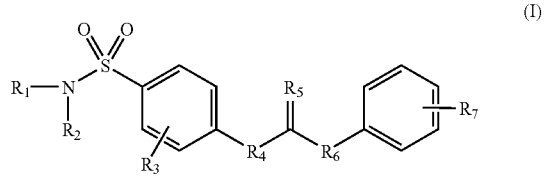

wherein $R_1$-$R_7$ are as defined in the description. Compounds (I) antagonize the vanilloid receptor and can be used for the preparation of medicaments for the treatment of inflammatory states.

23 Claims, No Drawings

SULFONAMIDO COMPOUNDS THAT ANTAGONIZE THE VANILLOID TRPV1 RECEPTOR

CROSS REFERENCE TO RELATED APPLICATIONS

The present application is a 35 U.S.C. §371 National Phase conversion of PCT/EP2005/011206 filed Oct. 18, 2005, which claims priority of Italian Application No. MI2004A002042 filed Oct. 26, 2004. The PCT International Application was published in the English language.

FIELD OF THE INVENTION

The present invention relates to antagonists of the vanilloid receptor, in particular to sulfonamido derivatives that antagonize the TRPV1 receptor.

BACKGROUND OF THE INVENTION

Recent experimental evidences have demonstrated that expression of the vanilloid TRPV1 receptor (transient receptor potential channel) increases in inflammatory conditions. This led to hypothesize that TRPV1 antagonists could be useful for the treatment of inflammatory processes, for example chronic pain and inflammatory hyperalgesia.

A number of antagonists of the vanilloid receptor are known; some of them derive from capsaicin and are called capsaicinoid antagonists. In particular, Wrigglesworth, R. et al (J. Med. Chem. 1996, 39, 4941-4951) disclosed the thiourea of formula (II):

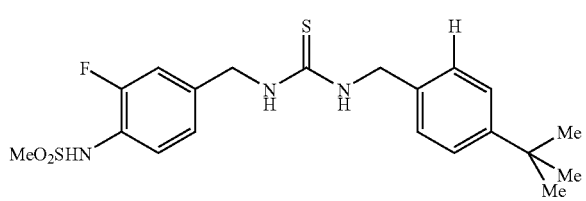

(II)

SUMMARY Of THE INVENTION

The present invention relates to compounds of general formula (I)

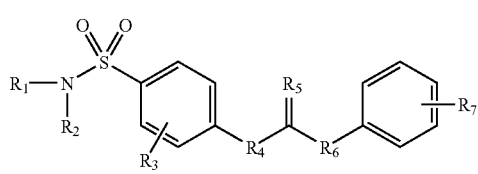

(I)

in which:

$R_1$ is hydrogen;

$R_2$ is benzyl or 2-phenylethyl, in which the aromatic ring is optionally substituted with one or more groups selected from halogen, hydroxy and methoxy;

$R_3$ is hydrogen, halogen or an alkoxy group;

$R_4$ is a —$(CH_2)_n$NH— group, in which n ranges from 0 to 3;

$R_5$ is S or O;

$R_6$ is —$NHCH_2$—;

$R_7$ is t-butyl or trifluoromethyl.

For the purposes of the present invention, halogen means fluorine, chlorine, bromine or iodine.

DETAILED DESCRIPTION OF CERTAIN EMBODIMENTS

Preferred compounds of formula (I) are those wherein $R_5$ is S and $R_6$ is a —$NHCH_2$— group, in particular those wherein $R_3$ is hydrogen and $R_7$ is selected from 4-t-butyl or 4-trifluoromethyl.

Among them, a first group of preferred compounds is that wherein $R_4$ n is 0.

A second group of preferred compounds is that wherein in the group $R_4$ n is 2; among them, particularly preferred are the compounds in which $R_1$ is hydrogen and $R_2$ is benzyl or 2-phenylethyl, optionally substituted as indicated above.

In the compounds of formula (I) in which $R_2$ is benzyl or 2-phenylethyl wherein the aromatic ring is substituted, those in which $R_2$ is 2-iodo-4-hydroxy-5-methoxy-benzyl are preferred.

The compounds of formula (I) proved active as inhibitors of the vanilloid TRPV1 receptor and can therefore be used for the preparation of pharmaceutical compositions for the therapy of inflammatory states, for example chronic pain and inflammatory hyperalgesia. These formulations will be prepared with conventional methods and excipients, such as those described in Remington's Pharmaceutical Sciences Handbook, XVII Ed. Mack Pub., N.Y., U.S.A.

The compounds of formula (I) can be conveniently prepared according to conventional known techniques, for example by reaction of a sulfonamide of formula (III):

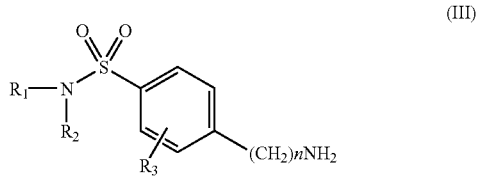

(III)

in which $R_1$, $R_2$, $R_3$ and n are as defined above;

with an isocyanate or an isothiocyanate of formula (IV)

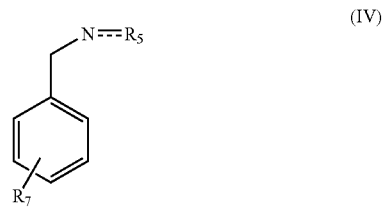

(IV)

The synthesis of some compounds of formula (I) is illustrated in Schemes 1-3 and is explained in greater detail in the following examples.
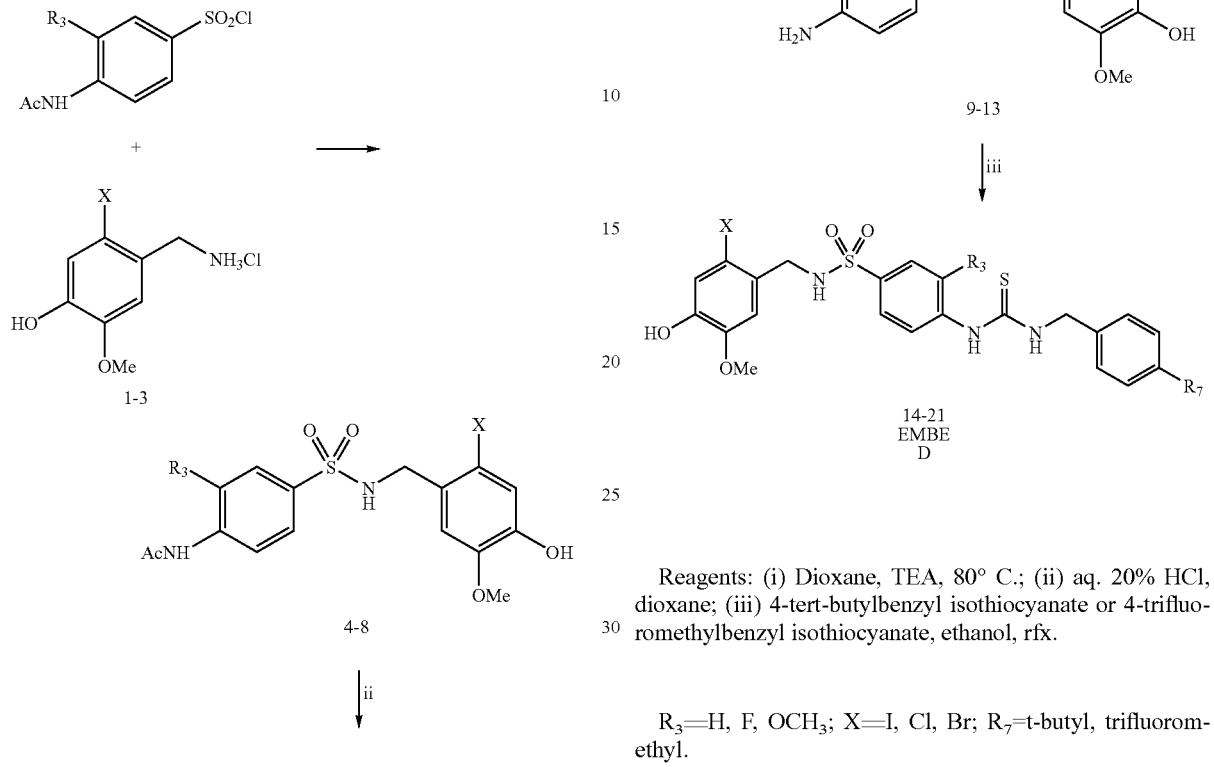
Reagents: (i) Dioxane, TEA, 80° C.; (ii) aq. 20% HCl, dioxane; (iii) 4-tert-butylbenzyl isothiocyanate or 4-trifluoromethylbenzyl isothiocyanate, ethanol, rfx.
$R_3$=H, F, OCH$_3$; X=I, Cl, Br; $R_7$=t-butyl, trifluoromethyl.
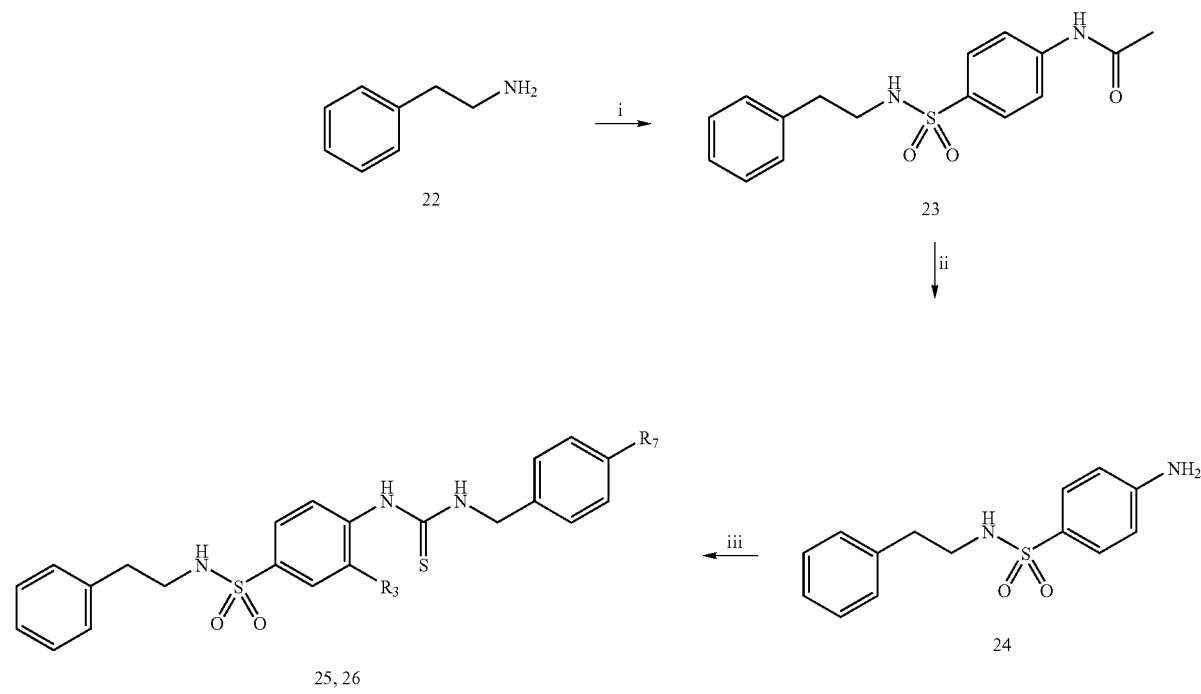

EMBEDReagents: (i) 4-acetamidobenzene sulfonyl chloride, dioxane; (ii) aq. 20% NaOH; (iii) 4-t-butylbenzyl isothiocyanate or 4-trifluoromethylbenzyl isothiocyanate.

$R_7$=t-butyl, trifluoromethyl.

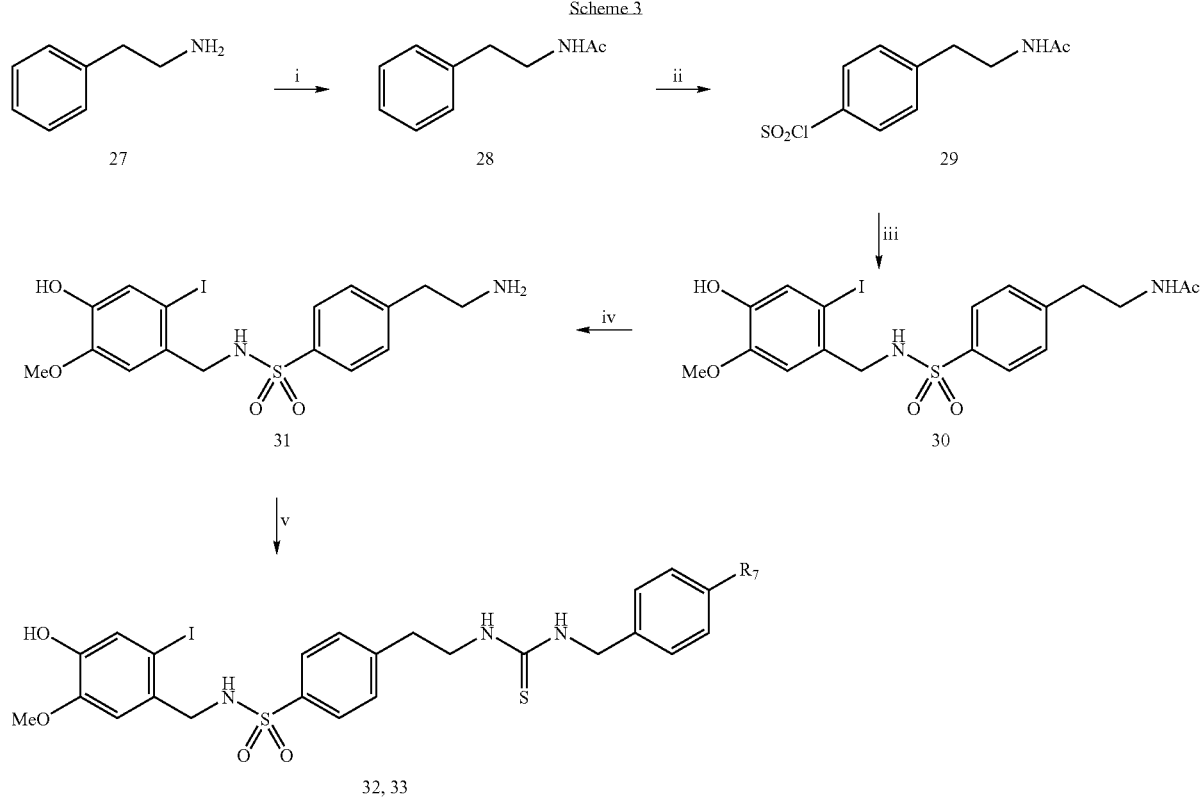

Scheme 3

EMBEDReagents: (i) Acetic anhydride, (ii) chlorosulfonic acid, 0° C.; (iii) 2-iodo(chloro,bromo)-5-methoxy-4-hydroxy benzylamine hydrochloride, dioxane; (iv) aq. 20% NaOH; (v) 4-tert-butylbenzyl isothiocyanate or 4-trifluoromethylbenzyl isothiocyanate, ethanol, rfx.

$R_7$=t-butyl, trifluoromethyl.

1. EXAMPLES

The following examples are provided only for the purpose of illustrating the invention and are not to be viewed as limiting the invention in any manner.

The reactions were routinely monitored by thin-layer chromatography (TLC) on silica gel (precoated $F_{245}$ Merck plates) and the products visualized with an iodine or potassium permanganate solution. $^1$H NMR spectra were recorded in $CDCl_3$, $CF_3COOD$ or DMSO-$d_6$ with a Varian VXR 200 spectrometer. Peak positions are given in parts per million (δ) downfield from tetramethylsilane as internal standard, and J values are given in Hz. IR spectra were recorded on a Pye Unicam SP 300 spectrometer using the KBr Wafer technique. Mass spectra were obtained with a Shimadzu QP5050 DI 50 spectrometer. The expression "Light petroleum ether" refers to petroleum fraction boiling at 40-60° C. Melting points (M.p.) were determined on a Buchi-Tottoli instrument and are uncorrected. Chromatographies were performed using Merck 60-200 mesh silica gel. The synthesized compounds showed $^1$H NMR spectra in agreement with the assigned structures. Elemental analyses were within ±0.4% of the theoretical values for C, H, and N.

1. Preparation of 2-(substituted)-4-hydroxy-5-methoxy-benzylamine hydrochlorides 1-3

1.1. Synthesis of 4-acetyloxy-3-methoxy-N-acetyl-benzylamine

Acetic anhydride (1 ml, 10.5 mmol) was added to a solution of 4-hydroxy-3-methoxy-benzylamine hydrochloride (0.5 g, 2.63 mmol) in pyridine (5 ml) and the mixture was stirred at room temperature for 6 hours. The solvent was removed under reduced pressure and the residue was suspended in water (100 ml). The aqueous layer was extracted with ethyl acetate (3×20 ml) and the combined organic phases were anhydrified ($Na_2SO_4$) and evaporated under reduced pressure to afford the title compound as white solid (0.45 g, yield 75%).

$^1$H-NMR (CDCl$_3$) δ 2.01 (s, 3H, CH$_3$), 2.31 (s, 3H, CH$_3$), 3.81 (s, 3H, OCH$_3$), 4.38 (d, 2H, J=6, CH$_2$), 5.90 (bs, 1H, NH), 6.90 (m, 3H, aromatic). MS: m/z 238.1 (M$^+$Cl$_2$H$_{15}$NO$_4$).

1.2. Synthesis of 2-iodo-4-acetyloxy-5-methoxy-N-acetyl benzyl amine

The diacetyl derivative of example 1.1 and a catalytic amount of trifluoromethane sulfonic acid (5-6 drops) were added to a solution of IPy$_2$BF$_4$[1,2] (0.69 g, 6.9 mmol) in CH$_2$Cl$_2$ (40 ml). The resulting mixture was stirred at room temperature for 5 hours, then added with 10% aq. sodium thiosulfate until it became completely clear. The aqueous layer was extracted with CH$_2$Cl$_2$ (3×25 ml) and the organic phases were anhydrified (Na$_2$SO$_4$) and evaporated under vacuum. The residue was recrystallized from a mixture of CH$_2$Cl$_2$/Et$_2$O to afford the title compound as pale yellow solid (0.38 g, yield 65%).

$^1$H-NMR (CDCl$_3$) δ 2.06 (s, 3H, CH$_3$), 2.33 (s, 3H, CH$_3$), 3.82 (s, 3H, OCH$_3$), 4.41 (d, 2H, J=5.6, CH$_2$), 6.0 (t, 1H, NH), 7.04 (s, 1H, aromatic), 7.44 (s, 1H, aromatic).

Bidimensional NOESY (CDCl$_3$): coupling between the singlet at 7.44 ppm and the singlet at 2.33 ppm confirms that iodine is at the 2-position of the aromatic ring.

MS: m/z 364 (M$^+$C$_{12}$H$_{14}$INO$_4$).

1.3. Synthesis of 2-chloro-4-acetyloxy-5-methoxy-N-acetyl benzyl amine

N-chlorosuccinimide (3.15 mmol, 0.42 g) was added to a solution of 4-acetyloxy-3-methoxy-N-acetyl-benzylamine of Example 1.1 (0.5 g, 2.1 mmol) in dry DMF (6 ml) and the mixture was stirred for 30' at 0° C. and then for 16 hours at room temperature.

When water was added to the reaction (40 ml) the formation of a white precipitate was observed.

The solid was filtered off and washed twice with cold water (2×20 ml), then dried over P$_2$O$_5$ to afford the title compound as white solid (0.45 g, 83% yield).

$^1$H NMR (DMSO-d$_6$) δ 1.89 (s, 3H), 2.24 (s, 3H), 3.76 (s, 3H, OCH$_3$), 4.27 (d, 2H, CH$_2$, J=8), 7.09 (s, 1H, aromatic), 7.25 (s, 1H, aromatic), 8.35 (t, 1H, NH).

Bidimensional NOESY (DMSO-d$_6$): coupling between the singlet at 2.24 ppm and the singlet at 7.25 ppm confirms that chlorine is at the 2-position of the aromatic ring.

MS: m/z 272.1 (M$^+$Cl$_2$H$_{14}$ClNO$_4$).

1.4. Synthesis of 2-bromo-4-acetyloxy-5-methoxy-N-acetyl benzyl amine

N-bromosuccinimide (3.15 mmol, 0.42 g) was added to a solution of 4-acetyloxy-3-methoxy-N-acetyl-benzylamine of Example 1.1 (0.5 g, 2.1 mmol) in dry DMF (6 ml) and the mixture was stirred for 30' at 0° C. and then for 16 hours at room temperature.

When water was added to the reaction (40 ml) the formation of a white precipitate was observed.

The solid was filtered off and washed twice with cold water (2×20 ml), then dried over P$_2$O$_5$ to afford the title compound as white solid (0.46 g, 81% yield).

$^1$H NMR (DMSO-d$_6$) δ 1.90 (s, 3H), 2.49 (s, 3H), 3.76 (s, 3H, OCH$_3$), 4.26 (d, 2H, CH$_2$, J=8), 7.093 (s, 1H, aromatic), 7.39 (s, 1H, aromatic), 8.36 (t, 1H, NH).

Bidimensional NOESY (DMSO-d$_6$): coupling between the singlet at 2.49 ppm and the singlet at 7.39 ppm confirms that bromine is at the 2-position of the aromatic ring.

MS: m/z 315.1 (M$^+$C$_{12}$H$_{14}$BrNO$_4$).

1.5. Synthesis of 2-iodo(chloro,bromo)-4-hydroxy-5-methoxy-benzylamine hydrochloride 1-3

37% hydrochloric acid (0.2 ml) was added to a solution of 2-iodo(chloro,bromo)-4-acetyloxy-5-methoxy-N-acetyl-benzylamine (0.1 g, 0.27 mmol) in abs. ethanol (5 ml) and the mixture was refluxed for 12 hours. After cooling, the solvent was evaporated off under reduced pressure and the residue was recrystallized from dry acetone to afford the title compounds as pale yellow solid in quantitative yield.

2. Preparation of N-[(2-substituted-4-hydroxy-5-methoxy)-benzyl]aminosulfonyl benzene-3-R$_3$-4-acetamides 4-8

To a solution of 3-(substituted)-sulfonyl chloride (2.1 mmol) in dioxane (50 mL) was added TEA (2 mol eq) and 2-substituted-4-hydroxy-5-methoxy benzylamine hydrochlorides (2 mol eq). The mixture was heated at reflux for 3 h, the solvent was removed at reduced pressure and water (50 mL) was added to the residue. The solid formed was filtered off, dried and recrystallized from ethanol to give the desired products as white solids.

2.1. N-[(2-iodo-4-hydroxy-5-methoxy)-benzyl]aminosulfonyl benzene-4-acetamide 4

Yield 80%; mp.: 123° C.; $^1$H-NMR (DMSO$_{d6}$) δ: 3.11 (s, 3H), 3.76 (s, 3H), 3.88 (d, 2H, J=8), 6.61 (d, 2H, J=4), 6.80 (s, 1H), 7.11 (t, 1H), 7.15 (s, 1H), 7.23 (bs, 1H), 7.53 (d, 2H, J=4), 8.80 (bs, 1H).

2.2. N-[(2-chloro-4-hydroxy-5-methoxy)-benzyl] aminosulfonyl benzene-4-acetamide 5

Yield 68%; mp.: 132° C.; $^1$H-NMR (DMSO$_{d6}$) δ: 2.08 (s, 3H), 3.37 (s, 3H), 4.04 (d, 2H, J=8), 6.72 (s, 1H), 6.83 (s, 1H), 7.72 (s, 4H), 7.92 (t, 1H), 9.47 (bs, 1H), 10.30 (s, 1H).

2.3. N-[(2-bromo-4-hydroxy-5-methoxy)-benzyl] aminosulfonyl benzene-4-acetamide 6

Yield 72%; mp.: 129° C.; $^1$H-NMR (DMSO$_{d6}$) δ: 2.07 (s, 3H), 3.69 (s, 3H), 3.99 (d, 2H, J=8), 6.76 (s, 1H), 6.87 (s, 1H), 6.95 (t, 1H), 7.66 (s, 4H), 8.44 (bs, 1H), 9.71 (bs, 1H).

2.4. N-[(2-iodo-4-hydroxy-5-methoxy)-benzyl]aminosulfonyl benzene-3-fluoro-4-acetamide 7

Yield 96%; mp.: 211° C.; $^1$H-NMR (DMSO$_{d6}$) δ: 3.57 (s, 3H), 3.79 (s, 3H), 3.98 (d, 2H, J=7.8), 7.06 (s, 1H), 7.21 (s, 1H), 7.51 (m, 1H), 7.82 (m, 2H), 8.35 (bs, 2H), 10.08 (bs, 1H).

2.5. N-[(2-iodo-4-hydroxy-5-methoxy)-benzyl]aminosulfonyl benzene-3-methoxy-4-acetamide 8

Yield 81%; mp.: 208° C.; $^1$H-NMR (DMSO$_{d6}$) δ: 3.42 (s, 3H), 3.77 (s, 3H), 3.81 (s, 3H), 4.01 (d, 2H, J=7.8), 7.16 (s, 1H), 7.23 (s, 1H), 7.60 (m, 1H), 7.80 (m, 2H), 8.44 (bs, 2H), 9.98 (bs, 1H).

3. General procedure for the hydrolysis of the N-acetyl functionalities of example 2

To a solution of the acetyl derivatives of examples 2 (1 g) in dioxane (15 mL) was added aq. 20% HCl (20 mL) and the mixture was heated at reflux for 1 h. The solvent was removed at reduced pressure and water was added to the residue. The solution obtained was neutralized with aq. 20% NaOH and the solid formed was filtered off and washed with cold water (30 mL). The precipitate was dried and recrystallized from abs. ethanol to afford the free amino compounds as solids in a quantitative yield.

3.1. N-(2-iodo-4-hydroxy-5-methoxybenzyl)-4-aminobenzene sulfonamide 9

Pale yellow solid, mp.: 111° C.; $^1$H-NMR (DMSO$_{d6}$) δ: 3.74 (s, 3H), 3.90 (d, 2H), 5.10 (bs, 2H), 6.61 (d, 2H, J=4), 6.83 (s, 1H), 7.00 (t, 1H), 7.16 (s, 1H), 7.50 (d, 2H, J=5), 8.80 (s, 1H).

3.2. N-(2-chloro-4-hydroxy-5-methoxybenzyl)-4-aminobenzene sulfonamide 10

Pale yellow solid, mp.: 111° C.; $^1$H-NMR (DMSO$_{d6}$) δ: 3.69 (s, 3H), 3.87 (d, 2H), 5.93 (bs, 2H), 6.56 (d, 2H, J=4), 6.73 (s, 1H), 6.85 (t, 1H), 7.41 (d, 2H), 7.56 (t, 1H), 9.22 (s, 1H).

3.3. N-(2-bromo-4-hydroxy-5-methoxybenzyl)-4-aminobenzene sulfonamide 11

Pale yellow solid, mp.: 115° C.; $^1$H-NMR (DMSO$_{d6}$) δ: 3.69 (s, 3H), 3.90 (d, 2H), 5.41 (bs, 2H), 6.63 (d, 2H, J=6), 6.87 (s, 1H), 6.90 (s, 1H), 7.46 (d, 2H, J=7), 7.64 (bt, 1H), 8.90 (bs, 1H).

3.4. N-(2-iodo-4-hydroxy-5-methoxybenzyl)-3-fluoro-4-aminobenzene sulfonamide 12

Pale yellow solid, mp.: 113° C.; $^1$H-NMR (DMSO$_{d6}$) δ: 3.72 (s, 3H), 3.88 (d, 2H), 5.88 (bs, 2H), 6.63 (d, 1H, J=4), 6.91 (s, 1H), 6.95 (s, 1H), 7.81 (m, 2H), 7.69 (t, 1H), 9.05 (bs, 1H).

3.5. N-(2-iodo-4-hydroxy-5-methoxybenzyl)-3-methoxy-4-aminobenzene sulfonamide 13

Yellow solid, mp.: 120° C.; $^1$H-NMR (DMSO$_{d6}$) δ: 3.44 (s, 3H), 3.77 (s, 3H), 3.94 (d, 2H), 6.01 (bs, 2H), 6.72 (d, 1H, J=4), 6.92 (s, 1H), 7.01 (s, 1H), 7.83 (m, 2H), 7.72 (t, 1H), 9.02 (bs, 1H).

4. General procedure for the synthesis of N-(4-R$_7$-benzyl)-N'-[4-(2-substituted)-4-hydroxy-5-methoxy-benzyl)-3-R$_3$-aminosulfonyl]phenyl thionrea derivatives 14-21

To a solution of compounds 9-13 (0.23 mmol) in abs. ethanol (10 mL) was added 4-t-butylbenzyl isothiocyanate or 4-trifluoromethylbenzyl isothiocyanate (1.2 mol eq, Wrigglesworth, R. et al. *J. Med. Chem.* 1996, 39, 4942-4951) and the mixture was refluxed for 16 h. The solvent was removed at reduced pressure and the residue was purified by flash chromatography (EtOAc:etere petrolio 1:1) to give derivatives 14-21 as solids.

4.1. N-(4-t-butyl-benzyl)-N'-[4-(2-iodo-4-hydroxy-5-methoxy-benzyl)aminosulfonyl]phenyl thiourea 14

Pale yellow solid, yield 42%, m.p.: 95° C.; $^1$H-NMR (CDCl$_3$) δ: 1.31 (s, 9H), 3.79 (s, 3H), 4.14 (d, 2H, J=4), 4.85 (d, 2H, J=4.2), 5.11 (t, 1H), 5.52 (bs, 1H), 6.75 (s, 1H), 7.05 (s, 1H), 7.27 (m, 4H), 7.41 (d, 2H), 7.74 (d, 2H), 7.86 (bs, 1H), 8.36 (bs, 1H). MS: m/z 640.6 (M$^+$C$_{26}$H$_{30}$IN$_3$O$_4$S$_2$). IR (KBr) cm$^{-1}$: 1548 (C=S). Anal. C, H, N, (C$_{26}$H$_{30}$IN$_3$O$_4$S$_2$): calculated C, 48.83; H, 4.73; N, 6.57. Found C, 48.80; H, 4.69; N, 6.55.

4.2. N-(4-trifluoromethyl-benzyl)-N'-[4-(2-iodo-4-hydroxy-5-methoxy-benzyl)aminosulfonyl]phenyl thiourea 15

Pale yellow solid, yield 38%, m.p.: 102° C.; $^1$H-NMR (DMSO$_{d6}$) δ: 3.69 (s, 3H), 3.88 (d, 2H, J=4), 4.76 (d, 2H, J=4), 6.51 (t, 1H), 6.69 (s, 1H), 7.05 (s, 1H), 7.36 (d, 2H), 7.44 (d, 2H), 7.55 (d, 2H), 7.63 (m, 3H), 7.81 (t, 1H), 9.37 (bs, 1H). MS: m/z 651.4 (M$^+$C$_{23}$H$_{21}$F$_3$IN$_3$O$_4$S$_2$). IR (KBr) cm$^{-1}$: 1550 (C=S). Anal. C, H, N, F (C$_{23}$H$_{21}$F$_3$IN$_3$O$_4$S$_2$): calculated C, 42.40; H, 3.25; N, 6.45; F, 8.75. Found C, 42.35; H, 3.22; N, 6.43; F, 8.76.

4.3. N-(4-t-butyl-benzyl)-N'-[4-(2-iodo-4-hydroxy-5-methoxy-benzyl)-3-fluoro-aminosulfonyl]phenyl thiourea 16

White solid, 41% yield, m.p.: 105° C.; $^1$H-NMR (DMSO$_{d6}$) δ: 1.29 (s, 9H), 3.62 (s, 3H), 3.83 (d, 2H, J=4), 4.13 (d, 2H, J=4.1), 6.44 (bt, 1H), 6.83 (s, 1H), 7.25 (m, 3H), 7.39 (m, 5H), 7.6 (bs, 1H), 7.80 (bs, 1H), 8.21 (bs, 1H). MS: m/z 658.5 (M$^+$C$_{26}$H$_{29}$FIN$_3$O$_4$S). Anal. C, H, N, F (C$_{26}$H$_{29}$FIN$_3$O$_4$S): calculated C, 47.49; H, 4.45; N, 6.39. Found C, 47.41; H, 4.44; N, 6.36.

4.4. N-(4-t-butylbenzyl)-N'-[4-(2-iodo-4-hydroxy-5-methoxy-benzyl)-3-methoxy-aminosulfonyl]phenyl thiourea 17

Pale yellow solid, 31% yield, m.p.: 103° C.; $^1$H-NMR (DMSO$_{d6}$) δ: 1.27 (s, 9H), 3.82 (s, 3H), 3.84 (s, 3H), 4.07 (d, 2H), 4.81 (m, 2H), 6.41 (bs, 1H), 6.85 (m, 2H), 7.16 (s, 1H), 7.26 (m, 6H), 7.52 (m, 2H), 8.05 (bs, 1H). MS: m/z 670.4 (M$^+$C$_{27}$H$_{32}$IN$_3$O$_5$S$_2$). Anal. C, H, N, F (C$_{27}$H$_{32}$IN$_3$O$_5$S$_2$): calculated C, 48.43; H, 4.82; N, 6.28. Found C, 48.40; H, 4.84; N, 6.25.

4.5. N-(4-t-butyl-benzyl)-N'-[4-(2-chloro-4-hydroxy-5-methoxy-benzyl)aminosulfonyl]phenyl thiourea 18

Pale yellow solid, 48% yield, m.p.: 124° C.; $^1$H-NMR (DMSO$_{d6}$) δ: 1.27 (s, 9H), 3.67 (s, 3H), 3.96 (m, 2H), 4.18 (d, 2H, J=6), 6.31 (t, 1H), 6.72 (s, 1H), 6.86 (s, 1H), 7.18 (d, 2H), 7.31 (m, 4H), 7.65 (s, 2H), 8.40 (t, 1H), 9.46 (s, 1H), 9.85 (bs, 1H). MS: m/z 549.4 (M$^+$C$_{26}$H$_{30}$ClN$_3$O$_4$S$_2$). Anal. C, H, N, F (C$_{26}$H$_{30}$ClN$_3$O$_4$S$_2$): calculated C, 56.97; H, 5.52; N, 7.67. Found C, 56.92; H, 5.50; N, 7.62.

4.6. N-(4-trifluoromethyl-benzyl)-N'-[4-(2-chloro-4-hydroxy-5-methoxy-benzyl)aminosulfonyl]phenyl thiourea 19

Yellow solid, 45% yield, m.p.: 122° C.; $^1$H-NMR (DMSO$_{d6}$) δ: 3.69 (s, 3H), 3.95 (d, 2H, J=6), 4.27 (d, 2H, J=6.1), 6.60 (t, 1H), 6.74 (s, 1H), 6.92 (m, 3H), 7.48 (d, 2H), 7.68 (m, 4H), 7.85 (t, 1H), 8.22 (bs, 1H), 9.41 (bs, 1H). MS: m/z 561.4 (M$^+$C$_{23}$H$_{21}$ClF$_3$N$_3$O$_4$S$_2$). Anal. C, H, N, F (C$_{23}$H$_{21}$ClF$_3$N$_3$O$_4$S$_2$): calculated C, 49.33; H, 3.78; N, 7.50; F, 10.18. Found C, 49.30; H, 3.74; N, 7.45; F, 1011.

4.7. N-(4-t-butyl-benzyl)-N'-[4-(2-bromo-4-hydroxy-5-methoxy-benzyl)aminosulfonyl]phenyl thiourea 20

Pale yellow solid, 51% yield, m.p.: 118° C.; $^1$H-NMR (DMSO$_{d6}$) δ: 1.29 (s, 9H), 3.58 (s, 3H), 3.81 (m, 2H), 4.19 (d, 2H, J=6), 6.22 (t, 1H), 6.81 (s, 1H), 6.91 (s, 1H), 7.23 (d, 2H), 7.40 (m, 4H), 7.69 (s, 2H), 8.43 (t, 1H), 9.49 (s, 1H), 10.01 (bs, 1H). MS: m/z 598.3 (M$^+$C$_{26}$H$_{30}$BrN$_3$O$_4$S$_2$). Anal. C, H, N, F (C$_{26}$H$_{30}$BrN$_3$O$_4$S$_2$): calculated C, 52.70; H, 5.10; N, 7.09. Found C, 52.66; H, 5.08; N, 7.12.

4.8. N-(4-trifluoromethyl-benzyl)-N'-[4-(2-bromo-4-hydroxy-5-methoxy-benzyl)aminosulfonyl]phenyl thiourea 21

Pale yellow solid, 49% yield, m.p.: 120° C.; $^1$H-NMR (DMSO$_{d6}$) δ: 3.62 (s, 3H), 4.01 (d, 2H, J=6), 4.35 (d, 2H, J=6.1), 6.63 (t, 1H), 6.81 (s, 1H), 6.90 (m, 3H), 7.55 (d, 2H), 7.72 (m, 4H), 8.01 (t, 1H), 8.42 (bs, 1H), 9.81 (bs, 1H). MS: m/z 605.3 (M$^+$C$_{23}$H$_{21}$BrF$_3$N$_3$O$_4$S$_2$). Anal. C, H, N, F (C$_{23}$H$_{21}$BrF$_3$N$_3$O$_4$S$_2$): calculated C, 45.70; H, 3.50; N, 6.95; F, 9.43. Found C, 45.63; H, 3.52; N, 6.92; F, 9.46.

5. Synthesis of N-(2-phenylethyl)-4-acetamidobenzene sulfonamide 23

A solution of sulfonyl chloride (0.5 g) in anhydrous dioxane (30 ml) is added with 2-phenylethyl-amine (1.6 eq, 0.43 ml) and the mixture is refluxed for about 1 hour. The solvent is removed under reduced pressure and the residue is taken up with water (35 ml). The resulting solid is filtered under reduced pressure, dried and crystallised from ethanol to give compound 23 a white solid. (0.61 g, 84% yield).

M.p.: 98° C. $^1$H-NMR (DMSO$_{d6}$) δ: 2.88 (s, 3H), 3.01 (t, 2H, J=8), 3.22 (q, 2H, J=8) 6.25 (t, 1H), 6.42 (d, 2H, J=6), 6.80 (m, 5H), 6.91 (bs, 1H), 7.01 (d, 2H, J=6).

6. Synthesis of N-(2-phenylethyl)-4-aminobenzene sulfonamide 24

To a solution of 23 (0.6 g, 1.7 mmol) in dioxane (8 ml) 20% NaOH is added (13 ml) and the mixture is refluxed for 1.5 hours. The solvent is concentrated under reduced pressure and the aqueous phase is added with 20% NaOH to pH=7. The resulting solid is filtered under reduced pressure, washed with water and dried to give compound 24 as white solid (0.43 g, 83% yield).

M.p.: 114° C. $^1$H-NMR (DMSO-d$_6$) δ: 2.2.75 (t, 2H, J=8), 3.3.20 (q, 2H, J=8), 4.4.18 (bs, 2H), 6.6.68 (d, 2H, J=6), 7.7.09 (d, 2H, J=5), 7.7.24 (m, 4H), 7.7.59 (d, 2H, J=6).

7. General procedure for the synthesis of N-(4-R$_7$-benzyl)-N'-[4-(2-phenylethyl-amino)sulfonyl]phenyl thioureas 25,26

A solution of compound 24 (150 mg) in absolute ethanol (12 ml) is added with t-butyl-benzyl isothiocyanate ((Wrigglesworth, R. et al. J. Med. Chem. 1996, 39, 4942-4951) or 4-trifluoromethyl benzyl isothiocyanate (1.2 eq) and the solution is refluxed for about 16 hours. The solvent is evaporated under reduced pressure and the residue is purified by chromatography (AcOEt:petroleum ether 1:1) to give compounds 25, 26 as solids.

7.1 N-(4-t-butyl-benzyl)-N'-[4-(2-phenylethyl-amino)-sulfonyl]phenyl thiourea 25

White solid, 40% yield, m.p.: 97° C. $^1$H-NMR (CDCl$_3$) δ: 1.30 (s, 9H), 2.77 (t, 2H, J=8), 3.22 (q, 2H, J=8), 4.61 (bs, 2H), 4.82 (d, 2H), 6.20 (bs, 1H), 7.08 (d, 2H) δ 7.25 (m, 5H), 7.37 (d, 2H), 7.77 (d, 2H), 7.82 (bs, 1H), 8.40 (bs, 1H). MS: m/z 481.1.1 (M$^+$C$_{26}$H$_{31}$N$_3$O$_2$S$_2$). Anal. C, H, N, S(C$_{26}$H$_{31}$N$_3$O$_2$S$_2$): calculated C, 64.83; H, 6.49; N, 8.72; S, 13.31. Found C, 64.80; H, 6.42; N, 8.69; S, 13.29.

7.2 N-(4-trifluoromethyl-benzyl)-N'-[4-(2-phenyletyl-amino)sulfosulfonyl]phenyl thiourea 26

White solid, 70% yield, m.p.: 102° C. $^1$H-NMR (CDCl$_3$) δ: 2.77 (t, 2H, J=6), 3.21 (q, 2H, J=6), 4.51 (t, 1H), 4.90 (d, 2H), 6.63 (d, 2H), 7.09 (d, 2H), 7.20 (m, 5H), 7.35 (d, 2H), 7.58 (d, 2H), 7.92 (bs, 1H), 8.32 (bs, 1H). MS: m/z 494.4.3 (M$^+$C$_{23}$H$_{22}$F$_3$N$_3$O$_2$S$_2$). Anal. C, H, N, F (C$_{23}$H$_{22}$F$_3$N$_3$O$_2$S$_2$): calculated C, 55.97; H, 4.49; N, 8.51; F, 1.1.55. Found C, 55.94; H, 4.47; N, 8.48; F, 11.52.

8. Synthesis of N-acetyl-2-phenylethylamine 28

A commercially available solution of 2-phenylethylamine (2 ml, 15.8 mmol) in pyridine (5 ml) is added with acetic anhydride (2 eq., 3 ml) and the solution is stirred at room temperature for 12 hours. The solvent is evaporated off under reduced pressure and the residue is taken up with water (40 ml) and the aqueous phase is extracted with EtOAc (4×25 ml). The organic extracts are pooled, anhydrified over Na2SO4 and evaporated under reduced pressure. The residue is crystallised from petroleum ether to give compound 28 as white solid (2.56 g, quantitative yield).

$^1$H-NMR (CDCl$_3$) δ: 1.93 (s, 3H), 2.81 (t, 2H, J=8), 3.51 (t, 2H, J=8), 5.61 (bs, 1H), 7.18 (m, 5H).

9. Synthesis of 4-acetamidoethylbenzene sulfonyl chloride 29

Compound 28 (0.5 g, 3 mmol) is added with HSO$_3$Cl (1.1 ml) drop by drop, keeping the temperature at 0° C. At the end of the addition the reaction mixture is heated to a 100° for about 1 hour, then cooled and poured over crushed ice. The resulting precipitate is filtered and washed with water to give compound 29 as white solid (0.51 g, yield 65%).

$^1$H-NMR (DMSO$_{d6}$) δ: 1.94 (s, 3H), 2.79 (t, 2H), 3.40 (m, 2H), 7.19 (d, 2H, J=4), 7.72 (d, 2H, J=4), 8.08 (bs, 1H).

10. Synthesis of N-[(2-iodo-4-hydroxy-5-methoxy)-benzyl]amino sulfonyl-benzene-N-ethyl-4-acetamide 30

A solution of 29 (250 mg, 0.9 mmol) in anhydrous dioxane (20 ml) is added with 2-iodo-4-hydroxy-5-methoxy benzylamine hydrochloride (1.6 eq, 480 mg) and TEA (1.8 eq, 0.24 ml) and the mixture is refluxed for about 1 hour. At the end of the addition the solvent is evaporated under reduced pressure and the residue is taken up with water (40 ml). The resulting precipitate is filtered with suction, washed with water and dried to give compound 30 as pale yellow solid (380 mg, yield 84%). The crude compound is used for the following deprotection reaction.

11. Synthesis of N-[(2-iodo-4-hydroxy-5-methoxy)-benzyl]-4-(2-ethylamino)benzene sulfonamide 31

A solution of compound 30 (110 mg, 0.22 mmol) in dioxane (5 ml) is added with 20% NaOH (6 ml) and the mixture is heated to 80° C. for about 3 hours. At the end of the addition the solvent is removed under reduced pressure and the pH of the residue is adjusted to 7 with 20% HCl. The resulting precipitate is filtered under reduced pressure, dried and e crystallised from ethyl ether to give compound 31 as pale yellow solid (90 mg, 88% yield).

M.p.: 291° C. $^1$H-NMR (DMSO$_{d6}$) δ: 2.48 (s, 3H), 2.67 (m, 2H), 3.52 (t, 2H), 3.67 (bs, 3H), 3.87 (s, 2H), 6.78 (s, 1H), 7.11 (s, 1H), 7.36 (d, 2H, J=8), 7.66 (d, 2H, J=8).

12=General procedure for the synthesis of N-(4-R$_7$-benzyl)-N'-[4-(2-iodo-4-hydroxy-5-methoxy-benzyl) aminosolfonyl-2-phenylethyl]thiourea derivatives 32 and 33

A solution of compound 31 (100 mg, 0.2 mmol) in absolute ethanol (12 ml) is added with 4-t-butyl-benzyl isothiocianate (Wrigglesworth, R. et al. J. Med. Chem. 1996, 39, 4942-4951) or 4-trifluoromethyl benzyl isothiocianate (1.2 eq.) and the solution is refluxed for about 16 hours. Thereafter, the solvent is evaporated under reduced pressure and the residue is purified by chromatography (EtOAc:petroleum ether 1:1) to give compounds 32 and 33 as solids.

12.1. N-(4-t-butyl-benzyl)-N'-[4-(2-iodo-4-hydroxy-5-methoxy-benzyl)aminosulfonyl-2-phenylethyl] thiourea 32

White solid, 41% yield, m.p.: 195° C. $^1$H-NMR (CDCl$_3$) δ: 1.31 (s, 9H), 2.85 (t, 2H), 4.71 (m, 2H), 3.79 (s, 3H), 4.14 (d, 2H, J=6), 4.49 (bs, 2H), 5.18 (t, 1H), 5.74 (bs, 1H), 5.91 (bs, 1H), 6.18 (bs, 1H), 6.70 (s, 1H), 7.2 (m, 5H), 7.37 (d, 2H), 7.66 (d, 2H). MS: m/z 668.5 (M$^+$C$_{28}$H$_{34}$IN$_3$O$_4$S$_2$). Anal. C, H, N(C$_{28}$H$_{34}$IN$_3$O$_4$S$_2$): calculated C, 50.37; H, 5.13; N, 6.29. Found C, 50.19; H, 5.11; N, 6.21.

12.2. N-(4-trifluoromethyl-benzyl)-N'-[4-(2-iodo-4-hydroxy-5-methoxy-benzyl)aminosulfonyl-2-phenyl-ethyl]thiourea 33

Pale yellow solid, 52% yield, m.p.: 186° C. $^1$H-NMR (CDCl$_3$) δ: 2.93 (t, 2H), 3.75 (m, 2H), 3.79 (s, 3H), 4.14 (d, 2H, J=8), 4.76 (d, 2H), 5.20 (t, 1H), 5.81 (bs, 1H); 5.92 (bs, 1H), 6.20 (t, 1H), 6.70 (s, 1H), 7.11 (s, 1H), 7.16 (d, 2H, J=6), 7.42 (d, 2H), 7.63 (m, 4H). MS: m/z 680.3 (M+C$_{25}$H$_{25}$F$_3$IN$_3$O$_4$S$_2$). Anal. C, H, N(C$_{25}$H$_{25}$F$_3$IN$_3$O$_4$S$_2$): calculated C, 44.19; H, 3.71; N, 6.18. Found C, 44.15; H, 3.52; N, 5.99.

2. Pharmacology

Materials and Methods

Animals and Tissues

Newborn and adult Sprague-Dawley rats (~250 g) were used (Harlam, Italy). All experiments complied with the national guidelines and were approved by the regional ethics committee.

Radioligand Binding Assays

Male Sprague-Dawley rats with body weight between 250 to 350 g at the time for testing were used. For binding assays rats were sacrificed by decapitation under anesthesia and spinal cord was removed and disrupted using a Polytron tissue homogenizer in ice cold buffer containing 5 mM KCl, 5.8 mM NaCl, 0.75 mM CaCl$_2$, 2 mM MgCl$_2$, 320 mM sucrose, 10 mM Hepes, pH 8.6 (Szallasi and Blunberg, 1992; 1993). Tissue homogenized was centrifuged at 1000×g for 10 min at 4° C. and the sumatant was centrifuged again at 35000×g for 30 min at 4° C. (Beckman Avanti J25). The pellet was resuspended in the same buffer as described above and used in binding experiments. In saturation experiments, 150 μg protein/sample from membrane suspensions were incubated with ([$^3$H]-Resiniferatoxin, Perkin Elmer, Boston, Mass.) [$^3$H]-RTX (0.003-3 nM) in the assay buffer containing 0.25 mg/ml fatty acid-free bovine serum albumin at 37° C. for 60 min. In competition experiments, the membranes were incubated at 37° C. for 60 min with [$^3$H]RTX (0.4 nM) and increasing concentrations of examined compounds in the range from 0.1 nM to 3 μM. Non specific binding was defined in the presence of 1 μM RTX. After incubation the reaction mixture was cooled at 0° C. and incubated with bovine α1-acid glycoprotein (200 μg per tube) for 15 min to reduce non-specific RTX binding. Membrane-bound RTX was separated from the free through the centrifugation of the samples at 18500×g for 15 min. The tip of the microcentrifuge tube containing the pellet was cut off and the radioactivity was determined by scintillation counting (Packard 2500 TR). The protein concentration was determined according to a Bio-Rad method with bovine serum albumin as a standard reference (Bradford, 1976). Saturation and competition studies were analyzed with the program Ligand (Munson and Rodbard, 1980).

Ca$^{2+}$ Fluorescence Measurements in Cultured Rat Trigeminal Ganglia Neurons

Newborn rats (2 days old) were terminally anaesthetized and decapitated. The trigeminal ganglia were removed and rapidly placed in cold phosphate buffered solution (PBS) before being transferred to collagenase/dispase (1 mg/ml dissolved in Ca$^{2+}$—Mg$^{2+}$-free PBS) for 35 min at 37° C. (Rigoni et al, 2003). After the enzymatic treatment ganglia were rinsed three times with Ca$^{2+}$—Mg$^{2+}$-free PBS and then placed in 2 ml of cold DMEM supplemented with 10% foetal bovine serum (FBS, heat inactivated), 2 mM L-glutamine, 100 u/ml penicillin and 100 mg/ml streptomycin. The ganglia were then dissociated into single cells by several passages through a series of syringe needles (23 G down to 25 G). Finally, the complex of medium and ganglia cells were sieved through a 40 mm filter to remove debris and topped up with 8 ml of DMEM medium and centrifuged (200×g for 5 min). The final cell pellet was re-suspended in DMEM medium (supplemented with 100 ng/ml mouse Nerve Growth Factor (mouse-NGF-7S) and cytosine-b-D-arabino-furanoside free base (ARA-C) 2.5 mM). Cells were plated on poly-L-lysine (8.3 mM) and laminin (5 mM) coated 25 mm glass cover slips and kept for 2 to 5 days at 37° C. in a humidified incubator gassed with 5% CO$_2$ and air. Plated neurons were loaded with Fura-2-AM-ester (3 μM) in Ca$^{2+}$ buffer solution of the following composition (mM): CaCl$_2$ 1.4, KCl 5.4, MgSO$_4$ 0.4, NaCl 135, D-glucose 5, HEPES 10 with BSA 0.1%, at pH 7.4, for 40 min at 37° C., washed twice with the Ca$^{2+}$ buffer solution and transferred to a chamber on the stage of Nikon eclipse TE300 microscope. The dye was excited at 340 and 380 nm to indicate relative [Ca$^{2+}$]$_i$ changes by the F$_{340}$/F$_{380}$ ratio recorded with a dynamic image analysis system (Laboratory Automation 2.0, RCS, Florence, Italy). Capsaicin (0.1 μM) and ionomycin (5 μM) were added to the chamber. A calibration curve using a buffer containing Fura-2-AM-ester and determinant concentrations of free Ca$^{2+}$ (Kudo et al., 1986) was used to convert the data obtained from F$_{340}$/F$_{380}$ ratio to [Ca$^{2+}$]$_i$ (nM).

The effects of all compounds were tested against capsaicin-induced calcium mobilisation. Antagonistic compounds were incubated for 10 minutes prior to the capsaicin challenge. The inhibitory effect of the TRPV1 antagonist, capsazepine, was also tested.

Wiping Test in Rats

The irritant effect (induction of wiping movements) of capsaicin was assessed by applying capsaicin 3 μg/eye (10 μl) on the rat conjunctiva and the number of wiping movements was recorded during the 60 sec period that followed the application. In other set of experiments, rats were treated intraperitoneally with diverse doses of 14 and capsaicin-induced wiping was studied.

Drugs and Solubility

Drugs and reagents were obtained from the indicated companies: capsaicin, ionomycin, laminin, poly-L-lysine and capsazepine (Sigma, Italy); mouse NGF-7S and collagenase/dispase (Roche Diagnostics, Italy); Dulbecco's Modified Eagle's medium (DMEM), foetal bovine serum (FBS) heat inactivated, L-glutamine (200 mM), penicillin/streptomycin (10,000 IU/ml±10,000 UG/ml), $Ca^{2+}$—$Mg^{2+}$-free phosphate buffered solution (PBS) (Gibco, Italy); Fura-2-AM-ester (Societa' Italiana Chimici, Italy). The stock concentrations of capsaicin (10 mM), were prepared in 100% ethanol. Mother solutions of all the PharmEste compounds (100 mM), Fura-2-AM-ester (100 mM) and ionomycin (100 mM) were prepared in DMSO. The appropriate dilutions were then made in Krebs buffer solution.

Results

General Overview

Compounds 14, 19 and 20 exhibited the ability to bind and activate the TRPV1 receptor.

Binding Assay

Competition binding experiments of [$^3$H]-RTX showed that 3 compounds had a great affinity versus the TRPV1 receptor expressed in rat spinal cord (table 1). In particular 14 revealed affinity values less than 100 nM. The order of potency of these compounds was: 14>20>19.

$Ca^{2+}$ Fluorescence

Capsaicin (0.1 μM) caused an increase in $[Ca^{2+}]_i$ in the vast majority (87%) of rat trigeminal neuronal cells, that therefore were identified as TRPV1 expressing neurons. For $IC_{50}$ values of all the compounds please referrer to table 1. Data are expressed as Mean and 95% fiducial limits.

TABLE 1

Affinities ($K_i$, nM) and potencies ($IC_{50}$, nM) values of TRPV1 antagonists

| Compound code | $K_i$ (nM) (Fiducial limits) | $IC_{50}$(nM) (Fiducial limits) |
| --- | --- | --- |
| Capsazepine | NT | 2168 (1528-3080) |
| 14 | 90 (73-110) | 60 (43-85) |
| 20 | 493 (340-716) | 212 (90-590) |
| 19 | 756 (515-1109) | 270 (127-574) |

Affinity ($K_i$) and potency ($IC_{50}$) values were obtained by using [$^3$H]-RTX competition binding assays and intracellular calcium assay in cultured rat trigeminal neurons. NT: not tested.

Wiping Test in Rats

Intraperitoneal compound 14, 60 minutes prior to the capsaicin challenge, caused a dose dependent reduction of the capsaicin-induced wiping behaviour in rats (the dose of 1 mg/kg produced a 24% of inhibition).

Conclusions

In in vitro and in vivo studies, 14 was able to inhibit TRPV1-dependent responses with an affinity that was significantly greater than that of the classic TRPV1 receptor antagonist, capsazepine. Furthermore, the compounds 19 and 20 did demonstrate high affinity for the TRPV1 receptor in vitro. All the compounds mentioned above may be an important tool for future studies in pain and neurogenic inflammatory models.

REFERENCES

Bradford M M, *Anal Biochem* (1976) 72: 248-254.
Kudo Y. et al., Japanese. Journal of Pharmacology (1986) 41, 345-151.
Munson P J et al., *Anal Biochem* (1980) 107: 220-239.
Rigoni M. et al., British Journal of Pharmacology (2003) 138, 977-985.
Szallasi A. and Blunberg P M, ed. P. M. Conn (Academic Press, Orlando, Fla.) (1992) vol. 8, p. 368.
Szallasi A. and Blunberg P M, *Naunyn Schmiedeberg's Arch Pharmacol* (1993) 347: 84-91.

What is claimed is:

1. A compound of formula (I):

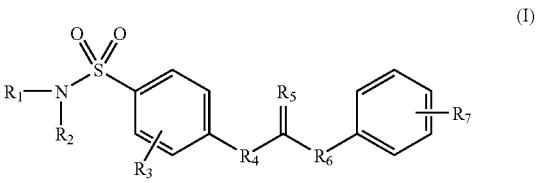

wherein:
$R_1$ is hydrogen;
$R_2$ is benzyl or 2-phenylethyl, wherein the aromatic ring is optionally substituted with one or more groups selected from halogen, hydroxy and methoxy;
$R_3$ is hydrogen, halogen or an alkoxy group;
$R_4$ is a —$(CH_2)_n$NH— group, wherein n ranges from 0 to 3;
$R_5$ is S or O;
$R_6$ is a —$NHCH_2$—; and
$R_7$ is t-butyl or trifuoromethyl.

2. The compound according to claim 1 wherein $R_5$ represents S and $R_6$ represents a —$NHCH_2$— group.

3. The compound according to claim 2 wherein $R_3$ is hydrogen, $R_7$ is selected from 4-t-butyl or 4-trifuoromethyl.

4. The compound according to claim 3 wherein, in the $R_4$ group, n is 0.

5. The compound according to claim 3 wherein, in the $R_4$ group, n is 2.

6. The compound according to claim 5 wherein $R_1$ is hydrogen and $R_2$ is benzyl or 2-phenylethyl, wherein the aromatic ring is optionally substituted with one or more groups selected from halogen, hydroxy and methoxy.

7. The compound according to claim 1 wherein $R_1$ is hydrogen and $R_2$ 2-is iodo-4-hydroxy-5-methoxy-benzyl.

8. A medicament comprising at least one compound formula (I) as defined in claim 1.

9. A method for the preparation of a pharmaceutical composition for therapy of inflammatory states said method comprising including in said pharmaceutical composition a compound of formula (I) as defined in claim 1.

10. The method according to claim 9 wherein the inflammatory state is chronic pain or inflammatory hyperalgesia.

11. A pharmaceutical composition containing a compound of formula (I) as defined in claim 1 in admixture with at least one of a suitable excipient and a suitable vehicle.

12. A method for the preparation of a pharmaceutical composition for therapy of inflammatory states, said method comprising including in said pharmaceutical composition a compound of formula (I) as defined in claim 2.

13. A method for the preparation of a pharmaceutical composition for therapy of inflammatory states, said method comprising including in said pharmaceutical composition a compound of formula (I) as defined in claim 3.

14. A method for the preparation of a pharmaceutical composition for therapy of inflammatory states, said method comprising including in said pharmaceutical composition a compound of formula (I) as defined in claim 4.

15. A method for the preparation of a pharmaceutical composition for therapy of inflammatory states, said method comprising including in said pharmaceutical composition a compound of formula (I) as defined in claim 5.

16. A method for the preparation of a pharmaceutical composition for therapy of inflammatory states, said method comprising including in said pharmaceutical composition a compound of formula (I) as defined in claim 6.

17. A method for the preparation of a pharmaceutical composition for therapy of inflammatory states, said method comprising including in said pharmaceutical composition a compound of formula (I) as defined in claim 7.

18. A pharmaceutical composition containing a compound of formula (I) as defined in claim 2 in admixture with at least one of a suitable excipient and a suitable vehicle.

19. A pharmaceutical composition containing a compound of formula (I) as defined in claim 3 in admixture with at least one of a suitable excipient and a suitable vehicle.

20. A pharmaceutical composition containing a compound of formula (I) as defined in claim 4 in admixture with at least one of a suitable excipient and a suitable vehicle.

21. A pharmaceutical composition containing a compound of formula (I) as defined in claim 5 in admixture with at least one of a suitable excipient and a suitable vehicle.

22. A pharmaceutical composition containing a compound of formula (I) as defined in claim 6 in admixture with at least one of a suitable excipient and a suitable vehicle.

23. A pharmaceutical composition containing a compound of formula (I) as defined in claim 7 in admixture with at least one of a suitable excipient and a suitable vehicle.

* * * * *